United States Patent [19]

Kikumoto et al.

[11] 4,091,114

[45] May 23, 1978

[54] PHARMACEUTICALLY ACTIVE 2-OMEGA-AMINOALKOXYDIPHENYLMETHANES

[75] Inventors: Ryoji Kikumoto, Machida; Akihiro Tobe, Kawasaki; Shinji Tonomura, Tokyo; Hidenobu Ikoma, Kawasaki, all of Japan

[73] Assignee: Mitsubishi Chemical Industries Limited, Tokyo, Japan

[21] Appl. No.: 703,978

[22] Filed: Jul. 9, 1976

Related U.S. Application Data

[63] Continuation-in-part of Ser. No. 612,006, Sep. 10, 1975, abandoned.

[51] Int. Cl.$^2$ .................... C07C 93/06; A61K 31/13
[52] U.S. Cl. .................... 424/330; 260/293.83; 260/501.18; 260/501.19; 260/570 R; 424/267; 424/316
[58] Field of Search .................... 260/293.83, 501.18, 260/501.19, 570 R, 570.7 R; 424/267, 316, 330

[56] References Cited

U.S. PATENT DOCUMENTS

| | | | |
|---|---|---|---|
| 2,534,236 | 12/1950 | Cusic | 260/253 |
| 2,703,324 | 3/1955 | Benkley et al. | 260/570 X |
| 2,768,207 | 10/1956 | Cheney et al. | 260/570 |
| 2,966,518 | 12/1960 | Johnson | 260/570.7 |

OTHER PUBLICATIONS

Benson et al., "Tranquilizing and Antidepressant Drugs," p. 30 (1962).
Burger, "Medicinal Chemistry," Third Ed., Part II, pp. 1470 and 1658 (1970).

*Primary Examiner*—Robert V. Hines
*Attorney, Agent, or Firm*—Oblon, Fisher, Spivak, McClelland & Maier

[57] ABSTRACT

2-Omega-aminoalkoxydiphenylmethanes are prepared and shown to be useful antidepressants.

12 Claims, No Drawings

PHARMACEUTICALLY ACTIVE 2-OMEGA-AMINOALKOXYDIPHENYLMETHANES

CROSS REFERENCE TO RELATED APPLICATIONS

This application is a continuation-in-part of U.S. application Ser. No. 612,006, filed on Sept. 10, 1975 and now abandoned.

BACKGROUND OF THE INVENTION

1. Field of the Invention

This invention relates to 2-omega-aminoalkoxydiphenylmethanes which are pharmacologically active as antidepressants.

2. Description of the Prior Art

L. C. Cheney et al, J. Am. Chem. Soc., Vol. 71, 60–64 (1949) describes several diphenylmethanes containing substituents at the 2-position, including 2-dimethylaminoethoxy, 2-diethylaminoethoxy, 2-morpholinoethoxy, 2-(1-piperidyl)ethoxy, 2-isopropylaminoethoxy, 3-(1-piperidyl)propoxy, 3-dimethylaminopropoxy and 3-dibutylaminopropoxy. This references also indicates that 2-(2-aminoethoxy)diphenylmethanes and 2-(3-aminopropoxy)diphenylmethanes have antihistaminic and local anesthetic activity in animals but does not suggest any antidepressant behavior. Similarly, U.S. Pat. Nos. 2,768,207, 2,534,236 and 2,966,518 disclose 2-omega-aminoalkoxydiphenylmethanes. Particularly, the latter patent to Johnson discloses the compound bearing the closest relationship to those of this invention, 2-omega-dimethylaminopentoxydiphenylmethane, as well as 2-omega-dimethylaminopropoxy diphenylmethane. However, none of these prior art compounds is disclosed as having antidepressant activity and in fact the former has inferior antidepressant activity while the latter display no such activity.

SUMMARY OF THE INVENTION

Accordingly, it is an object of this invention to provide novel 2-omega-aminoalkoxydiphenylmethanes having superior antidepressant activity.

This and other objects of the present invention as will hereinafter become clear have been attained by providing compounds of the formula (I):

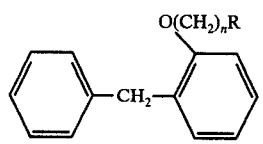

wherein R is selected from the group consisting of $C_1$–$C_5$ alkylamino and 1-piperidyl and $n$ is an integer of 4 or 5; and the pharmaceutically acceptable acid addition salts thereof. Also included is the case wherein $n = 3$ and R = methylamino.

This invention also relates to a method for palliating conditions of depression in warm-blooded animals which comprises administering to said animal an antidepressant effective amount of a compound of Formula I, and a method for producing said compound which comprises reacting an omega-halogenoalkoxydiphenylmethane of the formula (II):

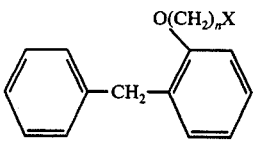

wherein X is halogen; and $n$ is as defined above, with an amine of the formula (III):

R—H        (III)

wherein R is as defined above.

DESCRIPTION OF THE PREFERRED EMBODIMENTS

As summarized above, this invention relates to a group of compounds useful as pharmaceutical agents, which compounds are represented by Formula I above.

Illustrative of the compounds of this invention are the following:

2-(4-methylaminobutoxy)diphenylmethane
2-(4-ethylaminobutoxy)diphenylmethane
2-(5-methylaminopentyloxy)diphenylmethane
2-(4-(1-piperidyl)butoxy)diphenylmethane
2-(3-methylaminopropoxy)diphenylmethane The pharmaceutically acceptable acid addition salts of the above compounds are, of course, also included within the scope of this invention. It will be understood that the term "pharmaceutically acceptable acid addition salts" as used herein is intended to include non-toxic salts of the compounds of this invention with an anion. Representative of such salts are hydrochlorides, hydrobromides, sulfates, phosphates, nitrates, acetates, succinates, adipates, propionates, tartrates, maleates, citrates, benzoates, toluenesulfonates, methanesulfonates and the like.

Of the compounds of this invention, it will be understood that the following compounds are most preferred due to their high level of antidepressant activity and their low level of toxicity.

2-(4-methylaminobutoxy)diphenylmethane
2-(4-ethylaminobutoxy)diphenylmethane
2-(5-methylaminopentyloxy)diphenylmethane.
Also preferred is 2-(3-methylaminopropoxy)diphenylmethane

PREPARATION

The compounds of this invention are prepared by reacting an omega-halogenoalkoxydiphenylmethane with an amine. The omega-halogenoalkoxydiphenylmethane starting materials which are represented by Formula II above can be prepared by reacting 2-hydroxydiphenylmethane with 1,4-dihalogenobutane or 1,5-dihalogenopentane in the presence of an alkali. The amine starting materials which are represented by Formula II above include ammonia; primary amines such as methylamine, ethylamine, isopropylamine and the like; secondary amines such as dimethylamine, diethylamine, N-methylethylamine and the like; morpholine; piperidine; and 4-methyl piperazine. The amine reacts with an equimolecular amount of the omega-halogenalkoxydiphenylmethane. However, the use of an excess of amine accelerates the reaction. Normally, the amount of the amine to be employed is in the range of from 1 to 100 moles per 1 mole of the omega-halogenoalkoxydiphenylmethane. The reaction can be carried out without an added solvent. However, the use of a reaction-inert solvent makes a homogeneous reaction possible. Examples of such solvents are water, dioxane, tetrahydrofuran, dimethyl sulfoxide, lower aliphatic alcohols and mixtures thereof. The reaction temperature is not critical, but normally ranges from room temperatures to 150° C. The reaction time varies widely with the reaction temperature and the reactivity of the starting materials, but normally is in the range of from 10 minutes to 40 hours.

The presence of a base which neutralizes the hydrogen halide formed in the course of the reaction accelerates the reaction. Examples of such bases are inorganic bases such as potassium hydroxide, sodium hydroxide, potassium carbonate, sodium carbonate and the like; and tertiary amines such as pyridine, triethylamine and the like. The amount of the base to be employed is normally in the range of from 1 to 5 moles per one mole of the omega-halogenoalkoxydiphenylmethane. When the base is absent, the omega-aminoalkoxydiphenylmethanes react with the hydrogen halide formed during the reaction, and are converted to the acid addition salts thereof.

Acid addition salts of the 2-omega-aminoalkoxydiphenylmethanes may be conveniently prepared by contacting the compounds with a suitable acid. The 2-omega-aminoalkoxydiphenylmethanes and the acid addition salts thereof may be purified by recrystallization employing a suitable solvent such as alcohol-ether.

Pharmacological testing of the 2-omega-aminoalkoxydiphenylmethanes has demonstrated that they are useful as antidepressant agents as evidenced by their ability to reverse reserpine hypothermia in mice. Anticonvulsant activity has also been displayed by the compounds of this invention. The compounds have been tested in mice for antidepressant, sedative, anticonvulsant and anticholinergic activity. The compounds were administered intraperitoneally and the activities of the compounds were compared with those of Amitriptyline. Antidepressant activity was evaluated by antagonism of reserpine (5 mg/kg i.p.) induced hypothermia (P. S. J. Spencer in "Antidepressant Drugs" S. Garattini and M. N. G. Duhes, ed., Excerpta Media Foundation, Amsterdam, pages 194–204 (1967)) and antireserpine activity was expressed as relative potency (Amitriptyline = 1). $LD_{50}$ was calculated by the Litchfield-Wilcoxon method. CNS depressant activity was defined by the ability of the compounds to cause neurological deficit as determined by a traction test (S. Courvoisier, R. Ducrot, L. Julou; "Psychotropic Drugs" ed. by S. Garattini, V. Ghetti, page 373, (1957)) and measurement of spontaneous motor activity. (Spontaneous motor activity was measured by the ANIMEX apparatus). Anticonvulsant activity was determined by antagonism of electroshock induced tonic extensor (L. S. Goodman, M. Singh Grewal, W. C. Brown and E. A. Swinyard, J. Pharmacol, Exptal. Therap., 108, 168 (1953)). Central anticholinergic effect was assessed by using the tremorine induced tremor in mice (G. M. Everett, L. E. Bloucus and J. M. Sheppard, Science 124 79 (1956)). Results are summarized in Table I and Table II, in which ED50 is defined as the dose of the test compounds which prevent 50% of each response.

Table I

Antireserpine Activity in Mice

| Compound | m.p. (° C) | Relative Potency | $LD_{50}$ (mg/kg i.p.) |
|---|---|---|---|
| Amitriptyline | | 1.00 | 65 |
| 2-(2-dimethylaminoethoxy)diphenylmethane hydrochloride [prior art] | 119–120 | 0 | |
| 2-(3-dimethylaminopropoxy)diphenylmethane hydrochloride [prior art] | 163–165 | 0 | |
| 2-(2-methylaminoethoxy)diphenylmethane hydrochloride [prior art] | 187–190 | 0 | |
| 2-(5-dimethylaminopentyloxy)diphenylmethane hydrochloride [prior art] | 87–91 | 0.23 | |
| 2-(3-methylaminopropoxy)diphenylmethane hydrochloride | 150–152 | 0.56 | |
| 2-(4-methylaminobutoxy)diphenylmethane hydrochloride | 114–119 | 0.73 | 173 |
| 2-(4-ethylaminobutoxy)diphenyl methane hydrochloride | 104–106 | 0.53 | 120 |
| 2-[4-(1-piperidyl)butoxy]diphenylmethane hydrochloride | 139–142 | 0.41 | |
| 2-(5-methylaminopentyloxy)-diphenylmethane hydrochloride | 87.5–89.5 | 0.54 | 160 |

Also tested for antireserpine activity as were the compounds of Table I were the following compounds, all of which are outside the scope of the present invention and all of which displayed a relative potency of 0: 2-(4-aminobutoxy) diphenylmethane hydrochloride (mp 112°–113° C); 2-(4-dimethylaminobutoxy) diphenyl methane hydrochloride (mp 135°–138° C); 2-(4-dimethylaminobutoxy) diphenyl methane hydrochloride (mp 173°–177° C); and 2-(4-(4-methyl-1-piperazinyl))-butoxy-diphenylmethane dihydrochloride.

Table II

CNS Depressant, Anticonvulsant and Central Anticholinergic Activity in Mice

| Compound | Anticonvulsant Activity ED50 (mg/kg i.p.) | Muscle Relaxant Action ED50 (mg/kg i.p.) | Spontaneous Motor Activity Depression ED50 (mg/kg i.p.) | Antitremorine Effect ED50 (mg/kg i.p.) |
|---|---|---|---|---|
| 2-(4-methylaminobutoxy)-diphenylmethane hydrochloride | 45 | 80 | 70 | >>60 |
| Amitriptyline | 16 | 15 | 18 | 4 |

It is apparent from Tables I and II that 2-(4-methylaminobutoxy)diphenylmethane exhibits antireserpine activity comparable to that of Amitriptyline, while it exhibits low toxicity, weak CNS depressant and anticholinergic action.

The compounds of this invention can be administered by any means that palliates conditions of depression in warm-blooded animals. For example, administration can be parenterally, subcutaneously, intravenously, intramuscularly, or intraperitoneally. Alternatively or concurrently, administration can be orally. The dosage administered will be dependant upon the age, health and weight of the recipient, the extent of depression, the kinds of concurrent treatment if any, the frequency of treatment, and the nature of the effect desired. Generally, a daily dosage of active ingredient compound will be from about 0.5 to 50 mg per kg of body weight. Normally, from 1 to 30 mg per kg per day, in one or more applications per day is effective to obtain the desired result. The compound of Formula I can be employed in dosage forms such as tablets, capsules, powder packets, or liquid solutions, suspensions, or elixirs, for oral administration, or sterile liquid formulations such as solutions or suspensions for parenteral use. In such compositions, the active ingredient will ordinarily always be present in an amount of at least 0.5% by weight based on the total weight of the composition and not more than 90% by weight.

In addition to the active ingredient of this invention, the composition can contain a solid or liquid non-toxic pharmaceutical carrier for the active ingredient. In one embodiment of a composition, the solid carrier can be a capsule of the ordinary gelatin type. In the capsule will be from about 30–60% by weight of a compound of Formula I and 70–40% of a carrier. In another embodiment, the active ingredient can be tableted with or without adjuvants, or put into powder packets. These capsules, tablets and powders will generally constitute from about 5% to about 95% and preferably from 25 to 90% by weight of active ingredient. These dosage forms preferably contain from about 5 to about 500 mg of active ingredient, with from about 25 to about 250 mg being most preferred. Suitable pharmaceutical carriers include sterile liquids such as water and oils, including those of petroleum, animal, vegetable or synthetic origin, such as peanut oil, soybean oil, mineral oil, sesame oil, and the like. In general, water saline, aqueous dextrose and related sugar solutions, and glycols such as ethylene glycol, propylene glycol and polyethylene glycol are preferred liquid carriers. Particularly for injectible solutions such as saline, the ordinary content of the active ingredient is from about 0.5 to 20% and preferably about 1 to 10% by weight.

As mentioned above, oral administration can be by a suitable suspension or syrup, in which the active ingredient normally will constitute from about 0.5 to 10% by weight. The pharmaceutical carrier in such compositions can be a watery vehicle such as an aromatic water, a syrup or a pharmaceutical mucilage.

Having generally described the invention, a more complete understanding can be obtained by reference to certain specific examples, which are included for purposes of illustration only and are not intended to be limiting unless otherwise specified.

EXAMPLE 1

A solution of 5.0 g of 2-(4-bromobutoxy)diphenylmethane, 20 ml of 40% dimethylamine aqueous solution, and 100 ml of ethanol is allowed to stand at room temperature for 8 hours. Ethanol and excess dimethylamine are distilled in vacuo, 2N-NaOH aqueous solution is added, and the reaction product is extracted with ether. The ether solution is distilled, 2N-HCl solution is added and the solution is evaporated to dryness. The residue is recrystallized from ethanol-ether to give 4.7 g (91% yield) of 2-(4-dimethylaminobutoxy)diphenylmethane hydrochloride m.p. 135°–138° C.

Analysis — Calcd. for $C_{19}H_{25}NO.HCl$ (percent): C, 71.34; H, 8.19; N, 4.38. Found (percent): C, 71.18; H, 8.21; N, 4.18.

EXAMPLE 2

A solution of 5.0 g of 2-(5-bromopentyloxy)diphenylmethane and 6 g of methylamine in 100 ml of ethanol is heated at a temperature of 50° C for 3 hours in a sealed tube. Ethanol and excess methylamine are distilled in vacuo, 2N-NaOH aqueous solution is added, and the reaction product is extracted with ether. Dry hydrogen chloride gas is passed into the ether solution, and the precipitate collected by filtration. Recrystallization from ethanol-ether gives 4.1 g (86% yield) of 2-(5-methylaminopentyloxy)diphenylmethane hydrochloride, m.p. 87.5°–89.5° C.

Analysis — Calcd. for $C_{19}H_{25}NO.HCl$ (percent): C, 71.34; H, 8.19; N, 4.38. Found (percent): C, 71.34; H, 8.30; N, 4.27.

EXAMPLES 3–5

The compounds in the following table were perpared according to the procedure described in Example 1 or 2, using the appropriate starting materials.

| Example No. | Formula | Addition Moiety | Preparation Process (Ex. No.) | m.p. (° C) | ANALYSIS Upper: Calcd. Lower: Found | | |
|---|---|---|---|---|---|---|---|
| | | | | | C | H | N |
| 3 | 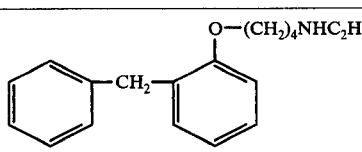 | HCl | 2 | 104–106 | 71.34<br>71.29 | 8.19<br>8.32 | 4.38<br>4.15 |
| 4 | 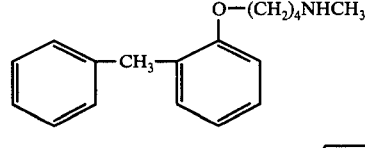 | HCl | 1 | 114–119 | 70.68<br>70.93 | 7.91<br>7.99 | 4.58<br>4.35 |
| 5 | 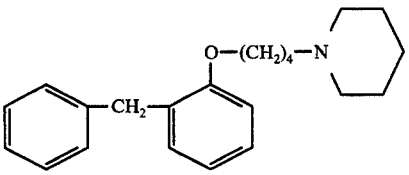 | HCl | 1 | 139–142 | 73.41<br>73.09 | 8.40<br>8.21 | 3.89<br>3.61 |

Having now fully described the invention, it will be apparent to one of ordinary skill in the art that many changes and modifications can be made thereto without departing from the spirit or scope of this invention as set forth herein.

What is claimed as new and intended to be covered by Letters Patent is:

1. A compound having the formula (I):

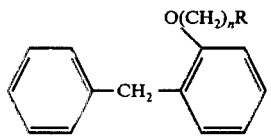

wherein R is selected from the group consisting of $C_1$–$C_5$ alkylamino, and 1-piperidyl and $n$ is an integer of 4 or 5; or a pharmaceutically acceptable acid addition salt thereof.

2. 2-(3-methylaminopropoxy) diphenylmethane or a pharmaceutically acceptable acid addition salt thereof.

3. The compound of claim 1, wherein R is methylamino or ethylamino.

4. The compound of claim 1 which is 2-(4-methylaminobutoxy) diphenylmethane.

5. The compound of claim 1, which is 2-(4-ethylaminobutoxy) diphenylmethane.

6. The compound of claim 1, which is 2-(5-methylaminopentyloxy)diphenylmethane.

7. The compound of claim 1, which is 2-(4-(1-piperidyl)butoxy) diphenylmethane.

8. A method for palliating conditions of depression in warm-blooded animals which comprises administering to said animal an antidepressant effective amount of a compound of the formula (I):

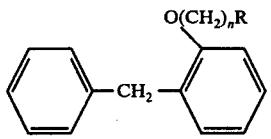

wherein R is selected from the group consisting of $C_1$–$C_5$ alkylamino, and 1-piperidyl and $n$ is an integer of 4 or 5; or wherein $n = 3$ and R is methylamino; or a pharmaceutically acceptable acid addition salt thereof.

9. A pharmaceutical composition comprising an antidepresent effective amount of a compound of claim 1 and a parmaceutically acceptable adjuvant.

10. A pharmaceutical composition comprising an antidepresent effective amount of a compound of claim 2 and a pharmaceutically acceptable adjuvant.

11. The compound of claim 1 wherein R is $C_1$–$C_5$ alkylamino.

12. The compound of claim 1 wherein when $n = 4$, R is $C_1$–$C_5$ alkylamino or 1-piperidyl and when $n = 5$, R is $C_1$–$C_5$ alkylamino.

* * * * *